(12) United States Patent
Boege et al.

(10) Patent No.: US 9,445,735 B2
(45) Date of Patent: Sep. 20, 2016

(54) ECG HAND-HELD DEVICE

(71) Applicant: Capical GmbH, Braunschweig (DE)

(72) Inventors: Henning Boege, Brauschweig (DE);
Martin Oehler, Braunschweig (DE);
Insa Kautzner, Brauschweig (DE);
Manfred Neumann, Braunschweig (DE)

(73) Assignee: Capical GmbH, Braunschweig (DE)

( * ) Notice: Subject to any disclaimer, the term of this patent is extended or adjusted under 35 U.S.C. 154(b) by 0 days.

(21) Appl. No.: 14/408,779

(22) PCT Filed: Jun. 18, 2013

(86) PCT No.: PCT/EP2013/062561
§ 371 (c)(1),
(2) Date: Dec. 17, 2014

(87) PCT Pub. No.: WO2013/189902
PCT Pub. Date: Dec. 27, 2013

(65) Prior Publication Data
US 2015/0190066 A1 Jul. 9, 2015

(30) Foreign Application Priority Data
Jun. 19, 2012 (DE) .......... 10 2012 105 306

(51) Int. Cl.
*A61B 5/0404* (2006.01)
*A61B 5/0402* (2006.01)
*A61B 5/044* (2006.01)
*A61B 5/0408* (2006.01)
*A61B 5/00* (2006.01)

(52) U.S. Cl.
CPC ......... *A61B 5/0404* (2013.01); *A61B 5/04085* (2013.01); *A61B 5/684* (2013.01); *A61B 5/742* (2013.01); *A61B 5/6801* (2013.01); *A61B 2562/0214* (2013.01); *A61B 2562/046* (2013.01); *A61B 2562/18* (2013.01); *A61B 2562/247* (2013.01)

(58) Field of Classification Search
USPC ......................................... 600/509
See application file for complete search history.

(56) References Cited

U.S. PATENT DOCUMENTS

| | | | |
|---|---|---|---|
| 4,606,352 A * | 8/1986 | Geddes | A61B 5/044 600/515 |
| 2004/0162587 A1* | 8/2004 | Hampton et al. | 607/5 |
| 2005/0017864 A1* | 1/2005 | Tsoukalis | 340/539.12 |

(Continued)

FOREIGN PATENT DOCUMENTS

| | | |
|---|---|---|
| DE | 10 2007 024 238 | 11/2008 |
| DE | 10 2009 019 242 | 11/2010 |
| GB | 1 442 296 | 7/1976 |

(Continued)

*Primary Examiner* — Carl H Layno
*Assistant Examiner* — Jon Eric C Morales
(74) *Attorney, Agent, or Firm* — Whitham, Curtis & Cook, P.C.

(57) ABSTRACT

An ECG device designed as a portable hand-held device, comprising a housing, on the outer face of which a plurality of ECG sensors in the form of capacitive electrodes is arranged in a sensor region, characterized by the following features: the EGG device has at least one flexible retaining mat in the sensor region, which retaining mat is designed to retain at least some or all ECG sensors, the retaining mat is made of liquid-tight material, at least some or all ECG sensors are fastened to the outer face of the retaining mat facing away from the housing.

20 Claims, 7 Drawing Sheets

(56) References Cited

U.S. PATENT DOCUMENTS

2006/0069320 A1 3/2006 Wolff et al.
2010/0292595 A1 11/2010 Paul

FOREIGN PATENT DOCUMENTS

| WO | WO 2011/084450 | 7/2011 |
| WO | WO 2012/019760 | 2/2012 |

* cited by examiner

ECG HAND-HELD DEVICE

FIELD OF THE INVENTION

The invention relates to an ECG device embodied as a portable handheld device.

In general, the invention relates to the detection of electrocardiograms (ECG) using ECG sensors in the form of capacitive electrodes. Capacitive electrodes allow an electrocardiogram to be measured with the same results as in the case of conventionally used galvanic electrodes. The advantage of capacitive electrodes lies in the fact that no direct skin contact is required, and so a measurement can even be performed through pieces of clothing.

BACKGROUND

The publication by Martin Oehler, Meinhard Schilling and Hans Dieter Esperer, Biomed Tech 2009; 54:329-335 has already disclosed a capacitive ECG system for measuring standard leads and for body surface potential maps.

WO 2012/019760 A1 proposes to fasten the ECG sensors to a foam block or to embed said ECG sensors into the foam block. Since the foam is not liquid-tight, it is additionally suggested to stretch a protective sleeve over the foam block and the ECG sensors arranged therein, said protective sleeve being liquid-tight, washable and wipe-disinfectable.

SUMMARY

The object underlying the present invention lies in improving the such ECG device in view of its producibility and its practical usability in medical everyday use.

In accordance with claim 1, this object is achieved by an ECG device embodied as a portable handheld device, comprising a housing, on the outer side of which a plurality of sensors in the form of capacitive electrodes are arranged in a sensor region, characterized by the following features:
a) in the sensor region, the ECG device includes at least one flexible holding pad, configured for holding at least some or all sensors,
b) the holding pad consists of liquid-tight material,
c) at least some or all sensors are fastened to the outer side of the holding pad facing away from the housing.

Therefore, in contrast to the proposition in accordance with WO 2012/019760 A1, a flexible holding pad configured for holding ECG sensors is now proposed. The holding pad consists of liquid-tight material. Some or all ECG sensors are fastened to the outer side of the holding pad facing away from the housing. An additional protective sleeve stretched over the ECG sensors and the foam block is not required as the holding pad consists of liquid-tight material. Instead, the holding pad already brings about a sufficient seal and therefore protection of the components arranged in the housing of the ECG device from liquids. A further advantage lies in the fact that the assembly of the ECG device can take place more easily and more quickly because the holding pad is already configured for holding the sensors and the latter can then simply be fastened to the holding pad. This allows significant saving of installation time during the production of the ECG device, particularly in the case of a relatively large number of ECG sensors, as are advantageous for the detection of spatially resolved electrocardiograms.

Moreover, the provision of a flexible holding pad improves the adaptability of the sensor region to the human body to be examined, e.g. the adaptability to different chest shapes. By way of example, the flexible holding pad can be elastic. By way of example, the flexible holding pad can be produced from an elastic material, e.g. polyurethane, silicone or latex.

The ECG sensors, which are embodied as capacitive electrodes, are connected to electrical components within the housing of the ECG device via electric lines or, possibly, via a common electric line. By way of example, the electric lines can be guided on the outer side of the holding pad on the surface thereof up to a point at the housing of the ECG device, where the lines are then passed through a housing wall. In an advantageous embodiment of the invention, the passage point of the lines through the housing wall likewise has a liquid-tight seal.

In accordance with an advantageous development of the invention, the ECG device includes the following features:
a) the holding pad includes at least one passage opening for electric lines,
b) at least one electric line is guided from at least one of the ECG sensors fastened to the holding pad into the housing of the ECG device through the passage opening.

An advantage of this is that the electric lines can be guided into the interior of the ECG device directly through the holding pad, and so a simple line run and short lines emerge. Firstly, this is advantageous from an electric and signaling point of view; moreover, this supports a simple and quick assembly of the multiplicity of ECG sensors and the electric connection thereof to the electrical components situated in the housing of the ECG device. The at least one electric line or the various electric lines are guided into the housing of the ECG device to an electronic circuit arranged therein through the passage opening or the plurality of passage openings in the holding pad. The electronic circuit can be used to record the signals from the ECG sensors and convert these into the ECG signals which, ultimately, are to be displayed.

By way of example, the electric lines of the ECG sensors can be embodied as laminated cables. These have a corresponding stiffness which allows the laminated cable to be guided in a quick and simple manner through the passage openings of the holding pad and, optionally, further passage openings of the housing of the ECG device.

In accordance with an advantageous development of the invention, the passage opening is sealed in a liquid-tight manner by at least one of the ECG sensors fastened to the holding pad. This is advantageous in that no additional component is required or needs to be assembled for sealing the passage opening. Instead, the seal can be brought about directly by the housing of an ECG sensor. Thus, for example, a ring-shaped elevation in the style of a wall surrounding the passage opening can be formed into the holding pad at a fastening point of an ECG sensor. If an ECG sensor is fastened to the fastening point, the housing of said sensor comes to rest on the ring-shaped elevation. The ring-shaped elevation then acts as a sealing ring at the same time. It is also possible to arrange a separate sealing ring between the ECG sensor and the holding pad at a fastening point for the ECG sensor surrounding the passage opening. Instead of the ring-shaped seal, a sealing pad may also be arranged between the ECG sensor and the holding pad.

Therefore, In accordance with an advantageous development of the invention, at least one sealing means configured for the liquid-tight sealing of the passage opening is arranged between an ECG sensor fastened to the holding pad and the holding pad.

In accordance with an advantageous development of the invention, provision is made for the holding pad to include a respective passage opening for each ECG sensor fastened to the holding pad, at least one electric line to be guided from each ECG sensor fastened to the holding pad into the housing of the ECG device through the respective passage opening and the passage opening of the respective ECG sensor to be sealed in a liquid-tight manner.

In accordance with an advantageous embodiment of the invention, the ECG sensors have a substantially square or rectangular cross section, possibly with rounded-off corners, in a plan view of the holding pad. Compared to sensors with a round cross section, this enables the best possible use of the available surface of the sensor region in the case of maximum signal generation by the capacitive electrodes. In accordance with an advantageous development of the invention, the ECG sensors are arranged on the holding pad with predetermined distances from one another, for example in the style of a matrix.

In accordance with an advantageous development of the invention, the housing of the ECG device includes a handle region and/or handle elements, wherein the handle region and/or the handle elements are configured to allow an operating person to hold the ECG device, wherein the holding pad is arranged outside of the handle region and the region of the handle elements. Thus, for example, the handle region can be provided on a rear side of the ECG device facing away from the sensor region; i.e., the holding pad is then provided on a front side of the ECG device. It is also possible for handle elements to be arranged laterally on the housing of the ECG device.

In accordance with an advantageous development of the invention, one, several or all of the ECG sensors include an electrically insulated sensor surface facing away from the holding pad. This avoids direct electric body contact when recording electrocardiograms, even in the case of unclothed body positions, and hence ensures reliable signal detection by the capacitive electrodes in every application situation of the ECG device. The electric insulation layer can be relatively thin, e.g. in the region of 0.2 μm. In accordance with an advantageous development of the invention, the electrical insulation of the sensor surface is embodied as a biocompatible lacquer coating of the sensor surface. This allows a simple, quick and cost-effective production of the ECG sensors. By way of example, the lacquer coating can be produced with parylene or from a polyurethane lacquer.

In accordance with an advantageous development of the invention, the holding pad is fastened on a layer of elastic damping material to the housing, which layer is arranged between the holding pad and a wall of the housing of the ECG device. By way of example, the damping material can be foam, in particular polyurethane foam or polyethylene foam. The layer made of the damping material can be embodied as a foam block.

Cold foam or a viscoelastic foam can be used as foam material. By way of example, latex can be used as viscoelastic material. Using viscoelastic foam is advantageous in that, firstly, the foam block can adapt well to the body shape of a patient and, as a result of the specific properties of the viscoelastic foam, said foam keeps its shape, once it is assumed, for a relatively long time as a result of the body heat and therefore adapts to the body shape in an adaptive manner. This is advantageous in that it is easier to handle the ECG device and, after an appropriate shape adaptation of the viscoelastic foam, said ECG device can be held against the patient with less application of force. Moreover, viscoelastic foam is easily processable, in particular at low temperatures.

In accordance with an advantageous development of the invention, one, several or all of the ECG sensors fastened to the holding pad are individually sprung in relation to the housing of the ECG device by means of at least one respective spring element. Such individual suspension by means of spring elements allows a particularly flexible adaptation of the sensor region of the ECG device to body shapes of patients.

A combination of the layer made of elastic damping material between the holding pad and the wall of the housing of the ECG device and the aforementioned individual spring elements is also advantageous. In this case, the layer made of elastic damping material may include appropriate bores, through which the spring elements are guided. By way of example, the spring elements can be supported at the wall of the housing of the ECG device. As a result of this combination, a spring/damping system with particularly expedient properties for the adaptability of the sensor region to different body shapes of patients can be created.

By way of example, the spring elements can be embodied as coil springs. Very different materials, such as plastic or steel, can be considered for the material of the spring elements. The use of a material with a spring effect which is as constant as possible, even at different temperatures, is advantageous since heating by the body temperature is to be expected during use of the ECG device on a patient.

In accordance with an advantageous development of the invention, the holding pad includes respective fastening points for one, several or all of the ECG sensors fastened to the holding pad, at which fastening points the ECG sensors are fastened to the holding pad, wherein one, several or all of the fastening points are respectively surrounded by a material region of the holding pad which has a greater flexibility than the material regions of the holding pad respectively adjoining this material region. In particular, a higher elasticity of the material of the holding pad can be provided in this region. Hence, the ECG sensors can be fastened to fastening points which are additionally movable with greater flexibility compared to the basic flexibility of the holding pad. This enables a flexible individual adaptation of the ECG sensors to the respective body shape of a patient. By way of example, the increased flexibility can be generated by the shaping of the holding pad in this material region, e.g. by a wave shape or by a reduced material thickness of the holding pad. In accordance with an advantageous development of the invention, the material region surrounding the fastening point can be embodied with greater flexibility in the style of bellows.

In accordance with an advantageous development of the invention, the holding pad includes respective fastening points for one, several or all of the ECG sensors fastened to the holding pad, at which fastening points the ECG sensors are fastened to the holding pad, wherein one, several or all of the fastening points are embodied as receptacle frames, in which in each case an ECG sensor is inserted. This enables a simple and quick assembly of the ECG sensors at the holding pad by virtue of said ECG sensors simply being inserted into the predetermined receptacle frames.

In accordance with an advantageous development of the invention, one, several or all of the receptacle frames are embodied in a trough-shaped manner.

In accordance with an advantageous development of the invention, the holding pad and the receptacle frame or frames for the ECG sensors are produced in a common injection molding process. This enables streamlined and cost-effective manufacturing of the holding pad with the receptacle frames. By way of example, the holding pad and the receptacle frames made of polyurethane material can be produced in a two-component injection molding method.

In accordance with an advantageous development of the invention, one, several or all of the receptacle frames have a greater material hardness than the regions of the holding pad surrounding the receptacle frames. In particular, the holding pad may have a greater Shore hardness in the regions surrounding the receptacle frames than the receptacle frames themselves. This enables, firstly, a flexible individual adaptation of the ECG sensors to the respective body shape of a patient and, secondly, a stable hold of the ECG sensors in the receptacle frames.

In accordance with an advantageous development of the invention, one, several or all of the receptacle frames include at least one latching means. An ECG sensor is fastened in the respective receptacle frame by the latching means. This allows streamlined and quick fastening of the ECG sensors to the holding pad by virtue of said ECG sensors only being inserted into the receptacle frames and latched therein. By way of example, the latching means can be embodied as inwardly pointing projections of the receptacle frame, in the style of latching lugs.

In accordance with an advantageous development of the invention, the ECG device includes at least one display means, which is configured to instruct a user to position the ECG device correctly on a patient on the basis of varying graphic display information. This enables simple operation of the ECG device, particularly also for persons who only have limited medical knowledge, such as e.g. first aiders at the site of an accident.

In accordance with an advantageous development of the invention, the ECG device includes at least one electric connection element for connecting at least one external ECG sensor. By way of example, the electric connection element can be embodied as a socket for receiving an electric plug-in connector. This is advantageous in that the ECG device can be expanded in terms of its function by external ECG sensors. By way of example, the external ECG sensor can be embodied as a capacitive electrode or as a conventional galvanic electrode.

In accordance with an advantageous development of the invention, the ECG device includes at least one electric connection element for connecting an external clamp electrode. By way of example, the clamp electrode can be used to establish potential equalization between a patient, on whom an ECG is intended to be recorded, and the ECG device.

In accordance with an advantageous development of the invention, the clamp electrode includes both a potential equalization contact and an external ECG sensor. The external ECG sensor and the potential equalization electrode are connectable to the ECG device by means of a common stranded connection cable. This allows an expansion of the function of the ECG device by means of an external ECG sensor and the potential equalization electrode, without a multiplicity of connection cables needing to be connected. This can avoid a "spaghetti of cables".

The invention also contains an external clamp electrode which includes both a potential equalization electrode and an external ECG sensor. The external ECG sensor is advantageously likewise embodied as a capacitive electrode.

In accordance with an advantageous development of the invention, at least one external ECG sensor is securely connected to the ECG device by means of a cable. Inside the housing, the ECG device includes a roll-up mechanism for the cable. This enables simple and quick storage of the cable, optionally together with the external ECG sensor, in the housing of the ECG device. As a result of this, the ECG device is manageable and easily transportable when not in use. A further advantage is that the external ECG sensor and the connection cable are always brought along and cannot be forgotten.

In accordance with an advantageous development of the invention, at least one satellite electrode arrangement is connectable to the ECG device, said satellite electrode arrangement including a plurality of ECG sensors in the form of capacitive electrodes. By way of example, use can be made of the capacitive electrodes in accordance with the above-described embodiments. To this end, the ECG device includes a connector which is configured for contacting the plurality of ECG sensors of the satellite electrode arrangement. The satellite electrode arrangement is advantageous in that it represents a type of external sensor pad, with which additional possibilities are provided within the scope of ECG signal detection, in particular with additional flexibility when handling and arranging the satellite electrode arrangement. The satellite electrode arrangement can have a similar embodiment to the ECG sensors arranged in the sensor region of the ECG device; by way of example, they can be embedded into a foam block fastened to a housing of a satellite electrode arrangement at said housing. Advantageously, the satellite electrode arrangement has a slightly smaller installation size than the ECG device.

By way of example, the satellite electrode arrangement can be connected like the above-described external ECG sensor.

In accordance with an advantageous development of the invention, the ECG device includes at least one capacitive equalization electrode. The capacitive equalization electrode serves for potential equalization. By way of example, the capacitive equalization electrode can be provided at the external ECG sensor or the satellite electrode arrangement, for example by virtue of one or more of the electrodes there being embodied as a capacitive equalization electrode.

In the following, the invention will be explained in more detail using drawings on the basis of exemplary embodiments.

BRIEF DESCRIPTION OF THE DRAWINGS

In detail.

In the figures, the same reference signs are used for corresponding elements.

DETAILED DESCRIPTION

Figure 1:
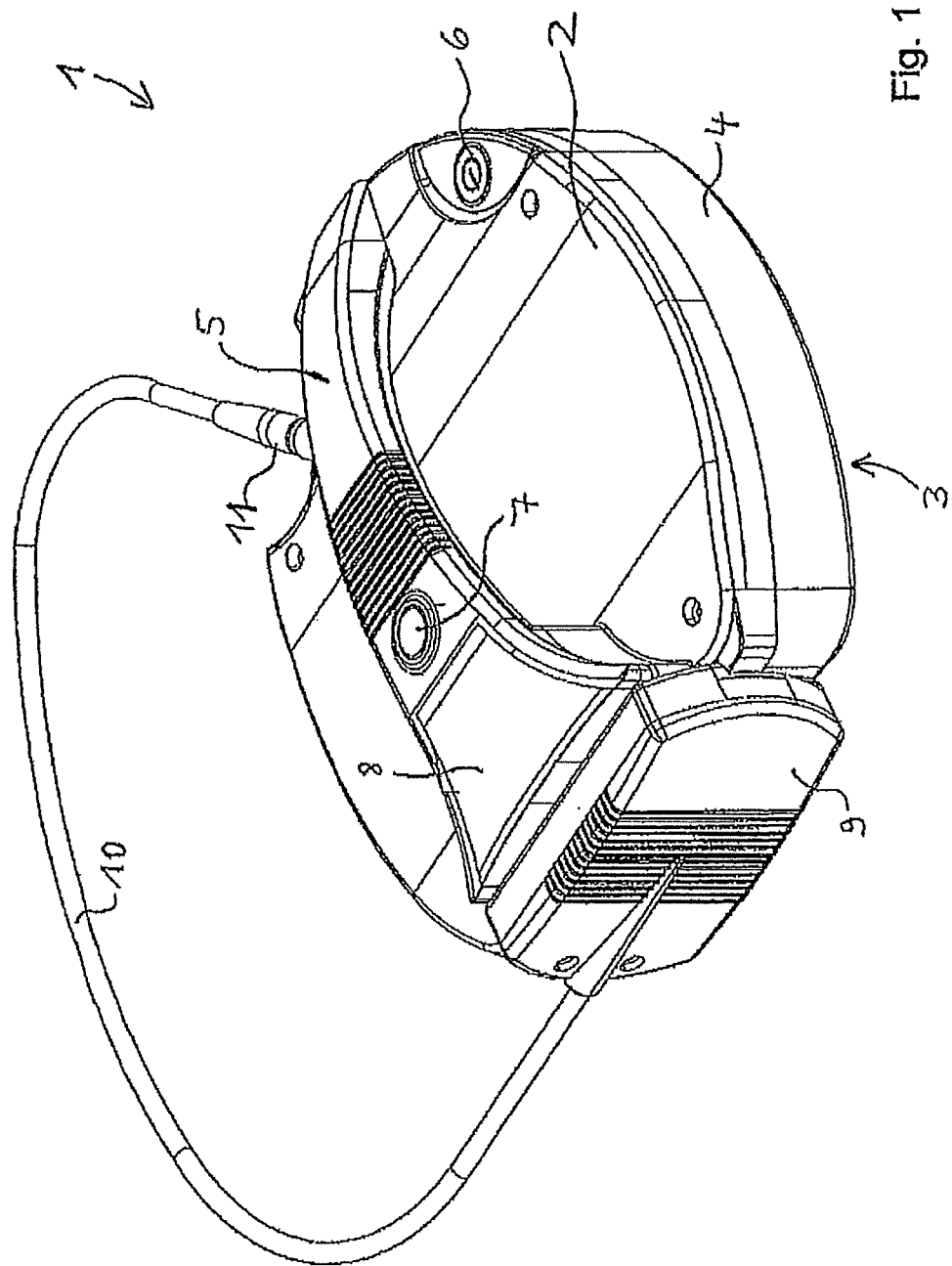
FIG. 1 shows a first view of an ECG device from the rear side.

FIG. 1 shows an ECG device 1 embodied as a portable handheld device, including a housing 2, on the outer side of which ECG sensors (not visible in FIG. 1) are arranged in a sensor region 3. The ECG sensors are fastened to the ECG device 1 by means of a flexible holding pad 4 which is pulled over the lateral edges of the housing 2. A handle 5 which is connected to the housing 2 is arranged on the rear side of the ECG device 1 facing away from the sensor region 3. An operating button 7 and a display apparatus 8, e.g. in the form of a display, are integrated into the handle 5. Moreover, a switch 6 serving to switch the ECG device 1 on and off is situated on the rear side of the housing 2. The ECG device 1 moreover includes a connector for an external sensor pad 9. The external sensor pad 9 can be connected to the ECG device 1 by means of a connection cable 10 and a plug-in connector 11. When not in use, the external sensor pad 9 can be latched onto, or clipped into, the housing 2 using corresponding latching means. By way of example, the external sensor pad 9 can be embodied as the aforementioned satellite electrode arrangement or the external ECG sensor described above.

Figure 2:
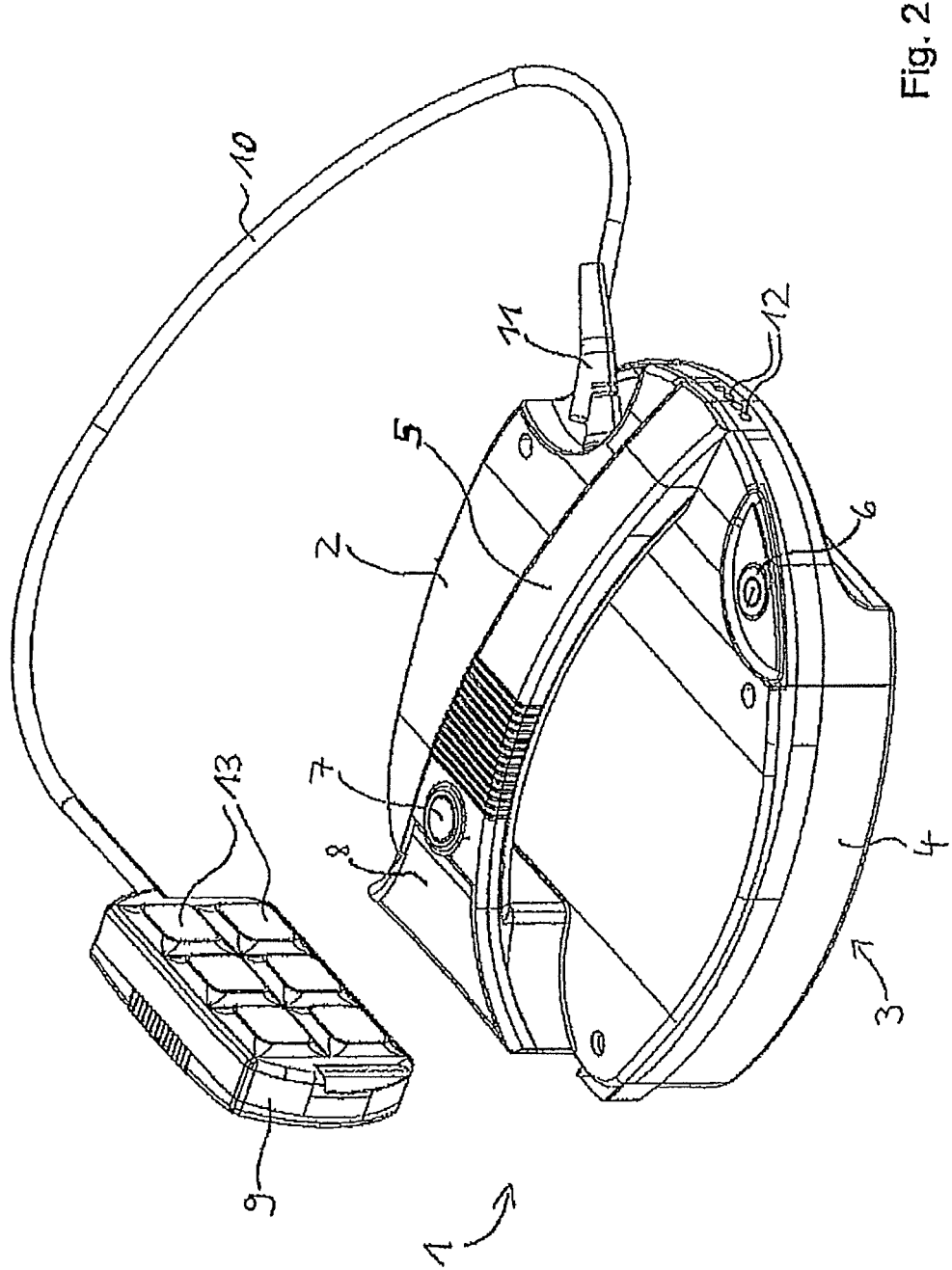
FIG. 2 shows a second view of the ECG device from the rear side.

FIG. 2 shows the ECG device 1 in accordance with FIG. 1 in a different view, likewise from the rear side. In the illustration in accordance with FIG. 2, the external sensor pad 9 has been taken off the housing 2. It is possible to identify that ECG sensors are arranged on the external sensor pad 9, for example six ECG sensors which are embodied as capacitive electrodes like the ECG sensors of the ECG device 1. The ECG sensors 13 are likewise fastened to the housing of the sensor pad 9 by means of a holding pad. The explanations below in respect of the holding pad 4 of the ECG device 1 and the ECG sensors thereof, as well as the attachment thereof, apply analogously to the external sensor pad 9 as well.

In FIG. 2, it is also possible to identify that the ECG device 1 includes electrical contacts 12 on a housing side on which the handle 5 merges into the housing 2. The electrical contacts 12 serve to connect the ECG device 1 to a charge device in order to charge a rechargeable battery present in the ECG device 1 for power supply purposes. By way of example, the ECG device 1 can be placed into a suitably shaped charge station leading with the contacts 12.

Figure 3:
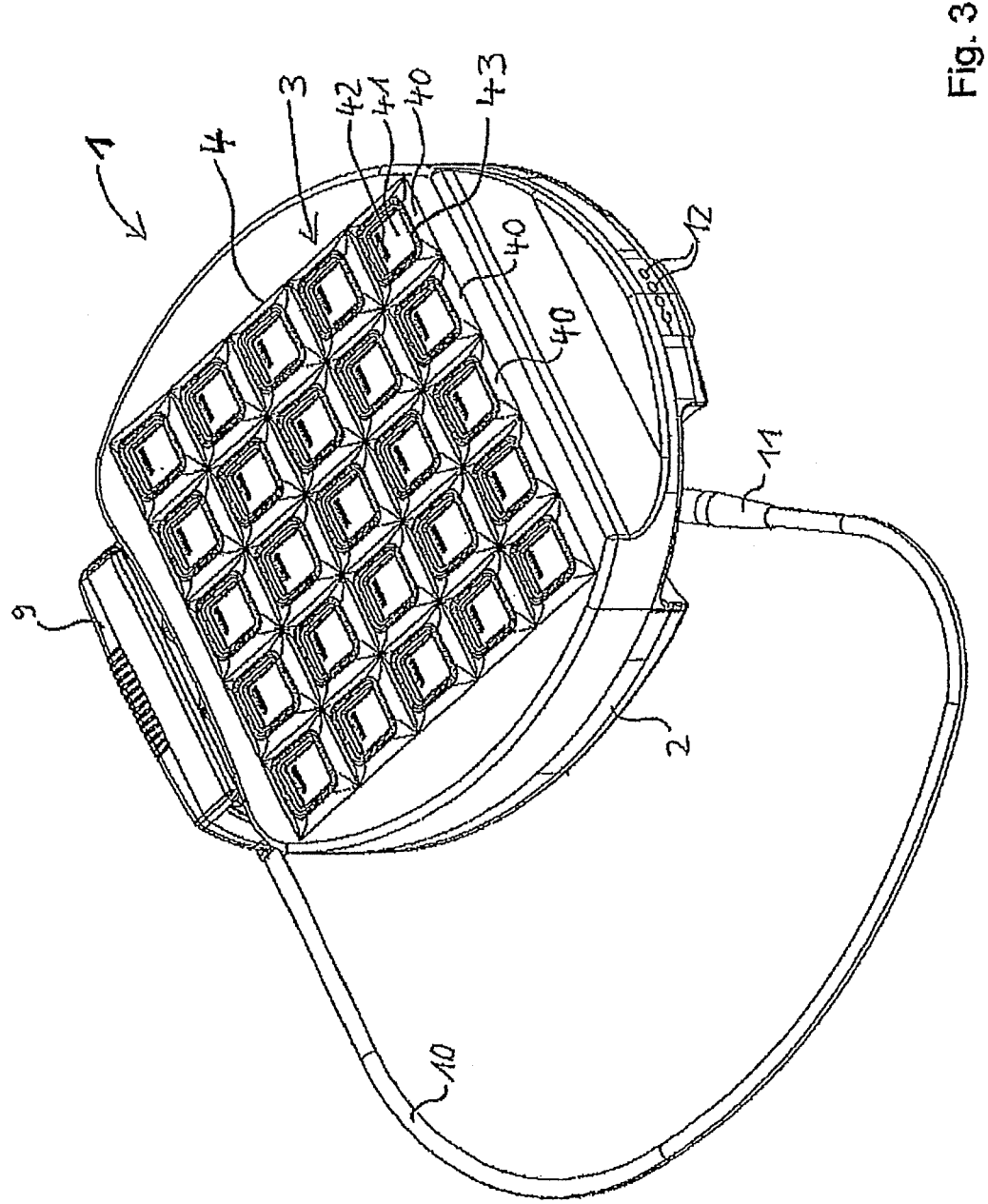
FIG. 3 shows a first view of the ECG device from a front side.

FIG. 3 shows the ECG device 1 with the external sensor pad 9 fastened thereto, in a view onto the sensor region 3 such that the holding pad 4 with fastening points 40, provided thereon, for the ECG sensors is visible. In FIG. 3, the holding pad 4 is still depicted without ECG sensors fastened thereto, and so the interior of the fastening points 40 can also be seen. By way of example, provision is made for 5×5=25 fastening points 40 for 25 ECG sensors. Each fastening point 40 includes a receptacle space 41 with a receptacle frame 43, into which an ECG sensor can be placed. In the respective receptacle space 41, the holding pad 4 includes a passage opening 42, through which electric lines of the ECG sensor are guided.

Figure 4:
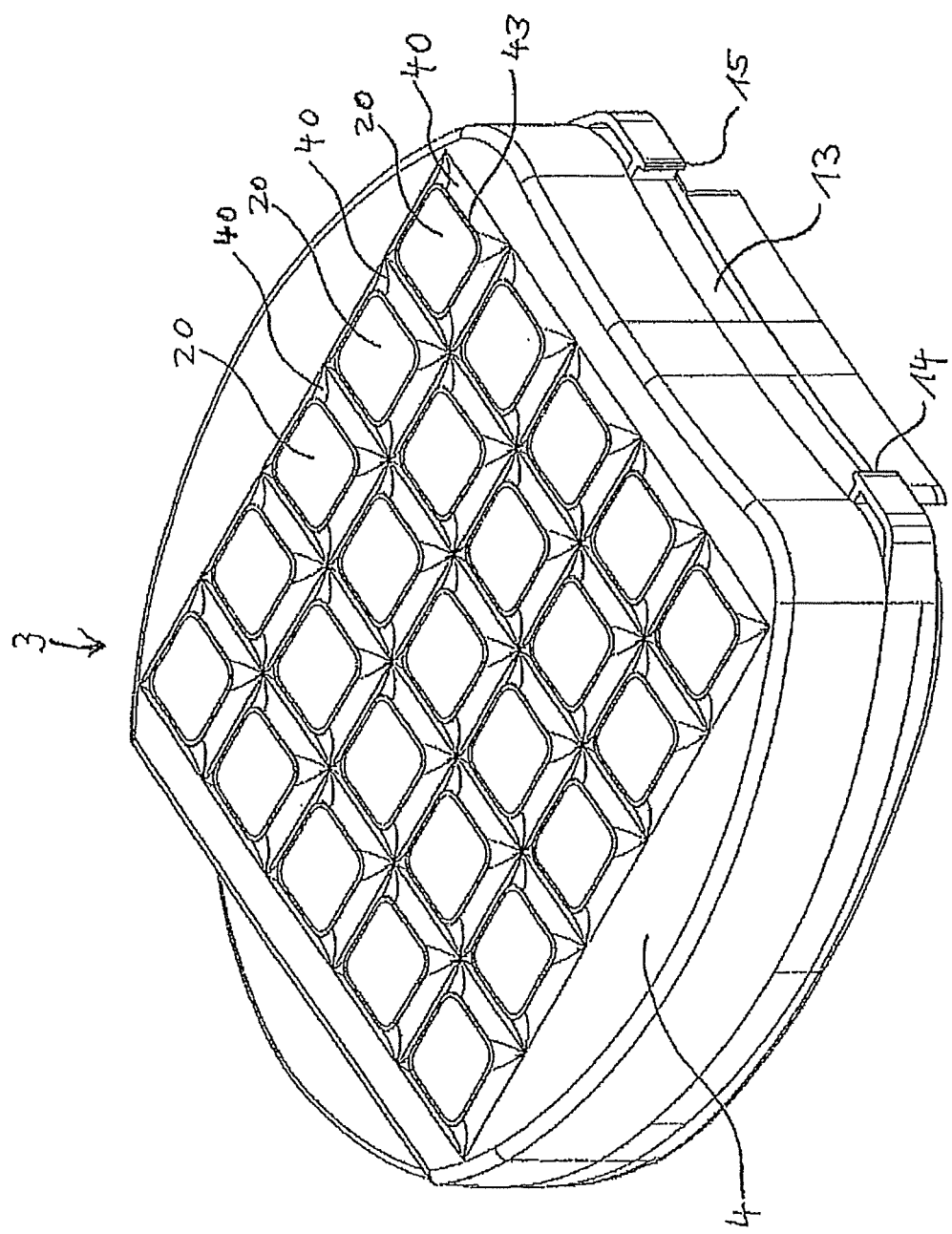
FIG. 4 shows a second view of the ECG device from the front side.

FIG. 4 shows a view of the ECG device 1, once again from the side of the sensor region 3 but with the external sensor pad 9 taken off. What can be seen is that a receptacle region 13 is present for receiving the sensor pad 9 on the housing 2 of the ECG device 1. It is possible to identify latching lugs 14, 15 at the housing 2, into which the external sensor pad 9 can be latched.

In accordance with FIG. 4, the holding pad 4 is moreover depicted with ECG sensors 20 arranged at the fastening points 40. The ECG sensors 20 lie substantially flush with the upper side of the fastening points 40 embodied in a mesa-like manner, and so an even surface results.

Figure 5:
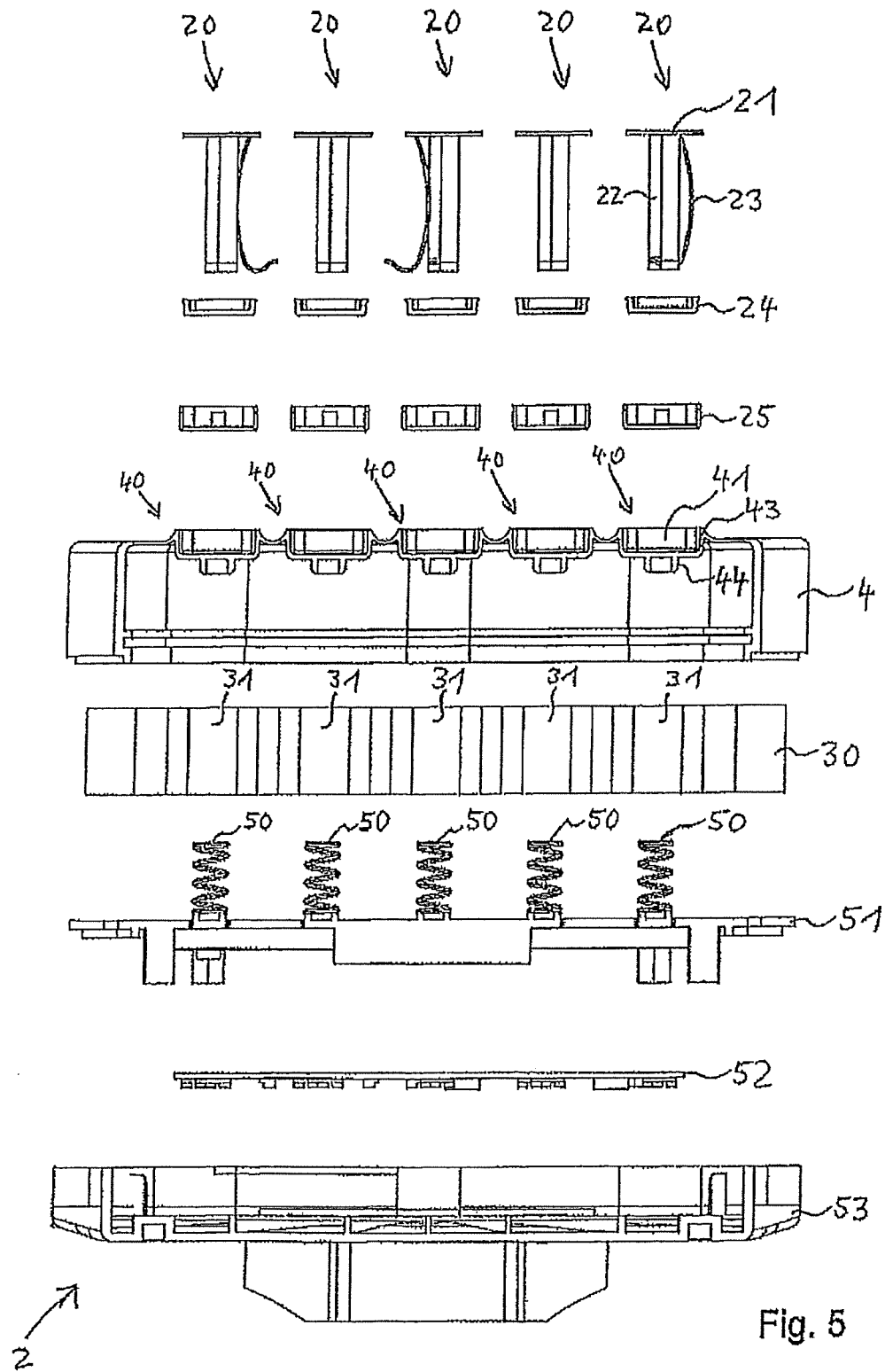
FIG. 5 shows the design of the ECG device in an exploded illustration.

FIG. 5 shows, in an exploded illustration, the design of the ECG device in a side view. It is possible to identify five ECG sensors 20, which each include a front-side sensor platelet 21, a holding body 24 for receiving the sensor platelet 21 and a cup-shaped sensor housing 25. The sensor platelets 21 each have electric lines 22, 23, which serve for electric contacting of the respective sensors 20. The sensor platelets 21 consist of electrically conducting material or include a layer made of such material, e.g. metal. On their outwardly pointing sides, the sensor platelets 21 are insulated, e.g. by a lacquer layer. The sensors 20 are embodied in the form of capacitive electrodes and can be designed as described in e.g. WO 2012/019760 A1.

The ECG sensors 20 assembled in this manner are inserted into the receptacle frames 43 and are held therein, e.g. by an interlock or due to a latching connection. As can be identified in FIG. 5, the holding pad 4 moreover includes, respectively at the side of a fastening point 40 facing away from the receptacle space 41, respective projections 44 which serve for holding and centering compression springs 50 in each case. The compression springs 50 can be preassembled on an outer wall of a housing component 51 of the housing 2 pointing toward the sensor region 3.

FIG. 5 moreover shows a layer 30 made of elastic damping material which is arranged between the housing component 51 and the holding pad 4. By way of example, the layer 30 can be embodied as a foam block or latex block. The layer 30 includes passage openings 31, through which the springs 50 are guided.

Furthermore, it is possible to identify that an electric printed circuit board 52 with electronic components is arranged in the housing 2, to be precise between the housing component 51 and a housing component 53. The electric printed circuit board 52 includes an evaluation circuit for evaluating the ECG signals received by the ECG sensors 20 and for forwarding the signals to an external visualization and storage apparatus.

Figure 6:
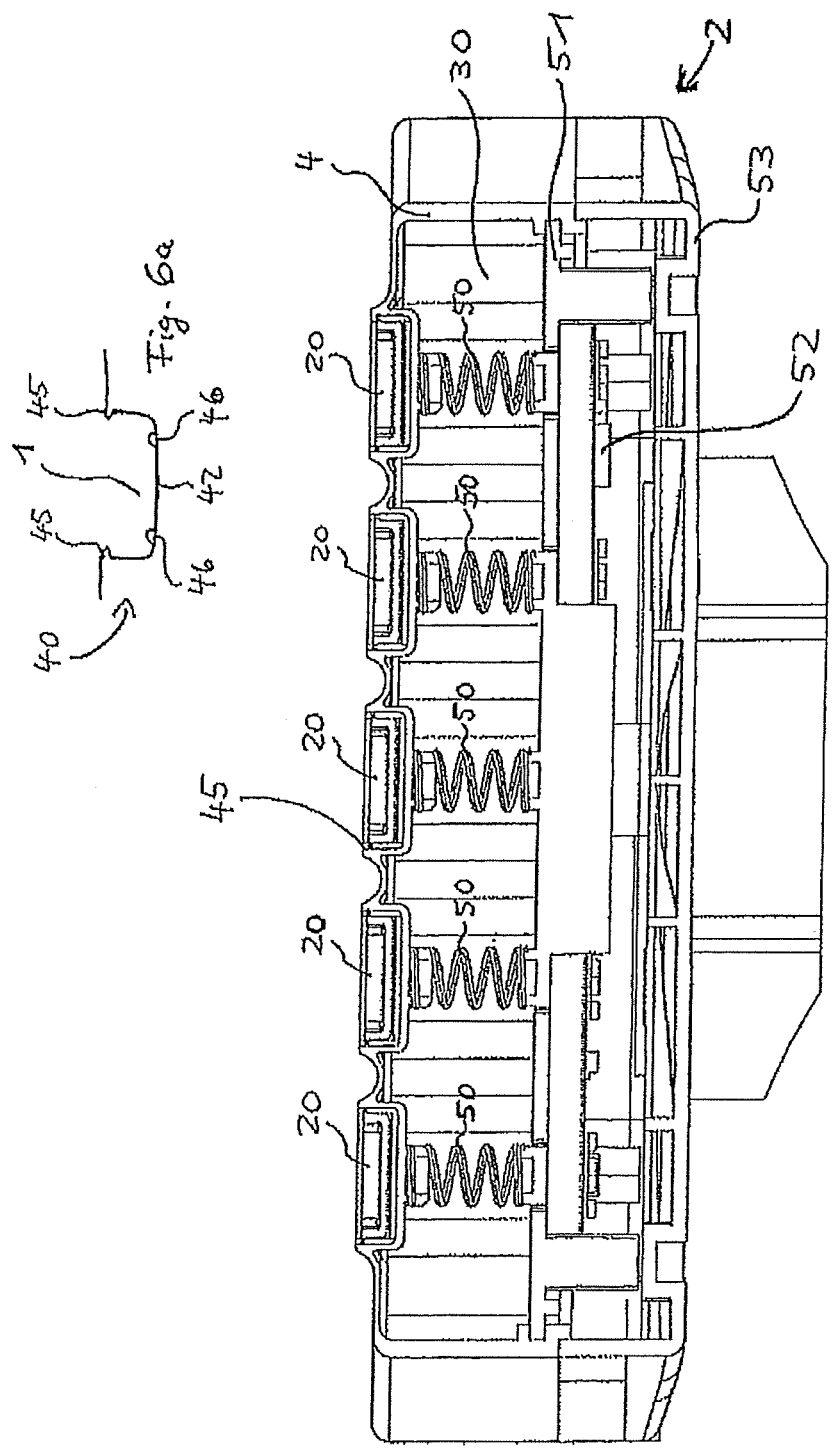
FIG. 6 shows a lateral section through the ECG device.

FIG. 6 shows the components explained on the basis of FIG. 5 in the assembled state, i.e. the complete ECG device 1 in a sectional illustration. Moreover, it is possible to identify, in particular on the basis of the detailed illustration in FIG. 6a, that each fastening point 40 may include sealing means 46 which are configured for sealing the passage opening 42 in a liquid-tight manner. The seal is effected by inserting an ECG sensor 20 into the receptacle space 41. The sensor 20 then comes to rest on the sealing means 46 and thereby brings about the liquid-tight seal of the passage opening 42. Furthermore, it is possible to identify in FIG. 6a that a receptacle space 41 may include lugs 45, by means of which a sensor 20 is held in the receptacle space 41 in the style of a latching connection, at the inner wall, for example the inner wall of the receptacle frame 43.

Figure 7:
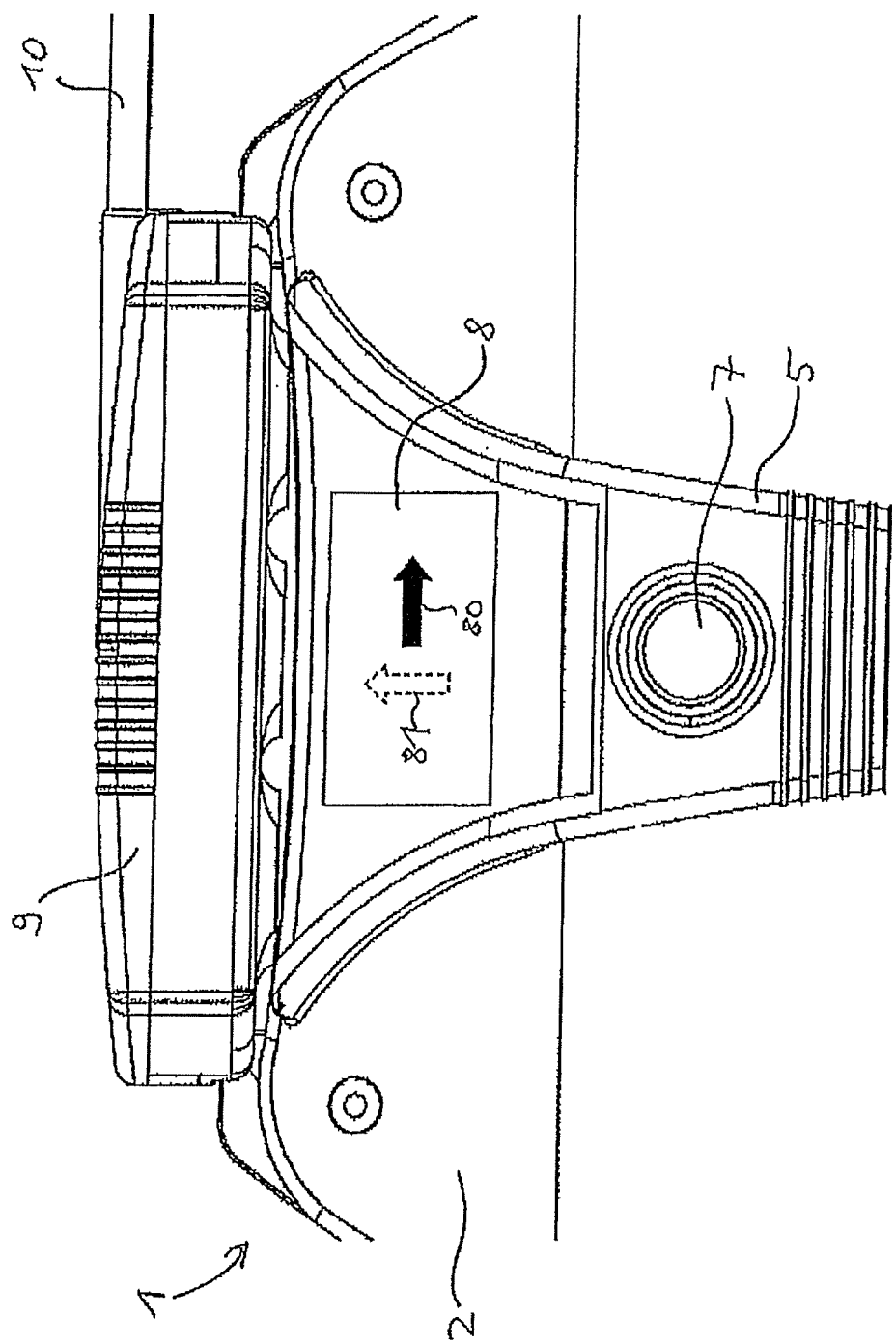
FIG. 7 shows a plan view of a detailed view of the rear side of the ECG device.

FIG. 7 shows the ECG device 1 in a section, wherein the display apparatus 8 in particular is depicted with further details. As is possible to identify, graphic display information, e.g. in the form of arrows 80, 81, can be depicted on the display apparatus 8, by means of which a user is instructed to position the ECG device 1 correctly on a patient.

The invention claimed is:

1. An ECG device, comprising
a housing in which circuitry is housed;
a plurality of ECG sensors in the form of capacitive electrodes arranged in a sensor region on an outer side of the housing;
at least one flexible holding pad in the sensor region, the at least one flexible holding pad being configured for holding at least some or all of the plurality of ECG sensors,
wherein the at least one flexible holding pad consists of liquid-tight material,
wherein at least some or all of the plurality of ECG sensors are fastened to the outer side of the at least one flexible holding pad facing away from the housing, wherein the ECG device is a portable handheld device during operation,
wherein one, several or all of the plurality of ECG sensors include an electrically insulated sensor surface facing away from the at least one flexible holding pad, and
wherein the electrical insulation of the sensor surface is a biocompatible lacquer coating of the sensor surface.

2. The ECG device as claimed in claim 1, wherein
a) the at least one flexible holding pad includes at least one passage opening for electric lines, and
b) at least one electric line is guided from at least one of the plurality of ECG sensors fastened to the at least one flexible holding pad into the housing of the ECG device through the at least one passage opening.

3. The ECG device as claimed in claim 1, wherein the housing includes a handle region and/or handle elements, wherein the handle region and/or the handle elements are configured to allow an operating person to hold the ECG device, wherein the at least one flexible holding pad is arranged outside of the handle region and the region of the handle elements.

4. The ECG device as claimed in claim 1, wherein one, several or all of the plurality of ECG sensors fastened to the at least one flexible holding pad are individually sprung in relation to the housing of the ECG device by means of at least one respective spring element.

5. The ECG device as claimed in claim 1, wherein the ECG device includes at least one display means, which is configured to instruct a user to position the ECG device correctly on a patient on the basis of varying graphic display information.

6. An ECG device, comprising
a housing in which circuitry is housed;
a plurality of ECG sensors in the form of capacitive electrodes arranged in a sensor region on an outer side of the housing;
at least one flexible holding pad in the sensor region, the at least one flexible holding pad being configured for holding at least some or all of the plurality of ECG sensors,
wherein the at least one flexible holding pad consists of liquid-tight material,
wherein at least some or all of the plurality of ECG sensors are fastened to the outer side of the at least one flexible holding pad facing away from the housing,
wherein the ECG device is a portable handheld device during operation,
wherein the at least one flexible holding pad includes respective fastening points for one, several or all of the plurality of ECG sensors fastened to the at least one flexible holding pad, at which fastening points the plurality of ECG sensors are fastened to the at least one flexible holding pad, wherein one, several or all of the fastening points are receptacle frames, in which in each case a respective one ECG sensor is inserted, and
wherein one, several or all of the receptacle frames are embodied in a trough-shaped manner.

7. The ECG device as claimed in claim 6, wherein
a) the at least one flexible holding pad includes at least one passage opening for electric lines, and
b) at least one electric line is guided from at least one of the plurality of ECG sensors fastened to the at least one flexible holding pad into the housing of the ECG device through the at least one passage opening.

8. The ECG device as claimed in claim 6, wherein the housing includes a handle region and/or handle elements, wherein the handle region and/or the handle elements are configured to allow an operating person to hold the ECG device, wherein the at least one flexible holding pad is arranged outside of the handle region and the region of the handle elements.

9. The ECG device as claimed in claim 6, wherein one, several or all of the plurality of ECG sensors fastened to the at least one flexible holding pad are individually sprung in relation to the housing of the ECG device by means of at least one respective spring element.

10. The ECG device as claimed in claim 6, wherein the ECG device includes at least one display means, which is configured to instruct a user to position the ECG device correctly on a patient on the basis of varying graphic display information.

11. An ECG device, comprising
a housing in which circuitry is housed;
a plurality of ECG sensors in the form of capacitive electrodes arranged in a sensor region on an outer side of the housing;
at least one flexible holding pad in the sensor region, the at least one flexible holding pad being configured for holding at least some or all of the plurality of ECG sensors,
wherein the at least one flexible holding pad consists of liquid-tight material,
wherein at least some or all of the plurality of ECG sensors are fastened to the outer side of the at least one flexible holding pad facing away from the housing,
wherein the ECG device is a portable handheld device during operation,
wherein the at least one flexible holding pad includes respective fastening points for one, several or all of the plurality of ECG sensors fastened to the at least one flexible holding pad, at which fastening points the plurality of ECG sensors are fastened to the at least one flexible holding pad, wherein one, several or all of the fastening points are receptacle frames, in which in each case a respective one ECG sensor is inserted, and
wherein the at least one flexible holding pad and the receptacle frame or frames for the ECG sensors are produced in a common injection molding process.

12. The ECG device as claimed in claim 11, wherein
a) the at least one flexible holding pad includes at least one passage opening for electric lines, and
b) at least one electric line is guided from at least one of the plurality of ECG sensors fastened to the at least one flexible holding pad into the housing of the ECG device through the at least one passage opening.

13. The ECG device as claimed in claim 11, wherein the housing includes a handle region and/or handle elements, wherein the handle region and/or the handle elements are configured to allow an operating person to hold the ECG device, wherein the at least one flexible holding pad is arranged outside of the handle region and the region of the handle elements.

14. The ECG device as claimed in claim 11, wherein one, several or all of the plurality of ECG sensors fastened to the at least one flexible holding pad are individually sprung in relation to the housing of the ECG device by means of at least one respective spring element.

15. The ECG device as claimed in claim 11, wherein the ECG device includes at least one display means, which is configured to instruct a user to position the ECG device correctly on a patient on the basis of varying graphic display information.

16. An ECG device, comprising
a housing in which circuitry is housed;

a plurality of ECG sensors in the form of capacitive electrodes arranged in a sensor region on an outer side of the housing;

at least one flexible holding pad in the sensor region, the at least one flexible holding pad being configured for holding at least some or all of the plurality of ECG sensors, wherein the at least one flexible holding pad consists of liquid-tight material, wherein at least some or all of the plurality of ECG sensors are fastened to the outer side of the at least one flexible holding pad facing away from the housing, wherein the ECG device is a portable handheld device during operation, wherein the at least one flexible holding pad includes respective fastening points for one, several or all of the plurality of ECG sensors fastened to the at least one flexible holding pad, at which fastening points the plurality of ECG sensors are fastened to the at least one flexible holding pad, wherein one, several or all of the fastening points are receptacle frames, in which in each case a respective one ECG sensor is inserted, and wherein one, several or all of the receptacle frames have a greater material hardness than the regions of the at least one flexible holding pad surrounding the receptacle frames.

17. The ECG device as claimed in claim 16, wherein
a) the at least one flexible holding pad includes at least one passage opening for electric lines, and
b) at least one electric line is guided from at least one of the plurality of ECG sensors fastened to the at least one flexible holding pad into the housing of the ECG device through the at least one passage opening.

18. The ECG device as claimed in claim 16, wherein the housing includes a handle region and/or handle elements, wherein the handle region and/or the handle elements are configured to allow an operating person to hold the ECG device, wherein the at least one flexible holding pad is arranged outside of the handle region and the region of the handle elements.

19. The ECG device as claimed in claim 16, wherein one, several or all of the plurality of ECG sensors fastened to the at least one flexible holding pad are individually sprung in relation to the housing of the ECG device by means of at least one respective spring element.

20. The ECG device as claimed in claim 16, wherein the ECG device includes at least one display means, which is configured to instruct a user to position the ECG device correctly on a patient on the basis of varying graphic display information.

* * * * *